United States Patent
Defrise et al.

(10) Patent No.: US 7,417,231 B2
(45) Date of Patent: Aug. 26, 2008

(54) FOURIER RE-BINNING OF TIME-OF-FLIGHT POSITRON EMISSION TOMOGRAPHY DATA

(75) Inventors: Michel Defrise, Brussels (BE); Michael E. Casey, Knoxville, TN (US); Christian J. Michel, Lenoir City, TN (US); Maurizio Conti, Knoxville, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 35 days.

(21) Appl. No.: 11/316,590

(22) Filed: Dec. 22, 2005

(65) Prior Publication Data

US 2006/0266946 A1 Nov. 30, 2006

Related U.S. Application Data

(60) Provisional application No. 60/638,532, filed on Dec. 22, 2004.

(51) Int. Cl.
*G01T 1/166* (2006.01)
(52) U.S. Cl. ................................ 250/363.04
(58) Field of Classification Search ............ 250/363.03, 250/363.04
See application file for complete search history.

(56) References Cited

U.S. PATENT DOCUMENTS

| | | | | |
|---|---|---|---|---|
| 5,378,893 | A * | 1/1995 | Murray et al. | 250/363.03 |
| 7,057,178 | B1 * | 6/2006 | Manjeshwar et al. | 250/363.04 |
| 7,227,149 | B2 * | 6/2007 | Stearns et al. | 250/363.03 |
| 2006/0102846 | A1 * | 5/2006 | Manjeshwar et al. | 250/363.03 |

OTHER PUBLICATIONS

Gregoire M.C., and Chesler D.A., Comparison of Two Fast Reconstruction Methods for a Cylindrical PET Camera, Oct. 25-31, 1992, Conference Record of the 1992 IEEE Nuclear Science Symposium and Medical Imaging Conference, vol. 2, pp. 907-909.*

Stearns C.W., Chesler D. A., and Brownell G.L., Accelerated Image Reconstruction for a Cylindrical Positron Tomograph Using Fourier Domain Methods, Apr. 1990, IEEE Transactions on Nuclear Science, vol. 37, No. 2, pp. 773-777.*

Defrise M., Kinahan P.E., Townsend D.W., Michel C., Sibomana M., and Newport D.F., Exact and Approximate Rebinning Algorithms for 3-D PET Data, Apr. 1997, IEEE Transactions on Medical Imaging, vol. 16, No. 2, pp. 145-158.*

* cited by examiner

*Primary Examiner*—David Porta
*Assistant Examiner*—David S Baker

(57) ABSTRACT

Fast reconstruction methods are provided for 3D time-of-flight (TOF) positron emission tomography (PET), based on 2D data re-binning. Starting from pre-corrected 3D TOF data, a re-binning algorithm estimates for each transaxial slice the 2D TOF sinogram. The re-binned sinograms can then be reconstructed using any algorithm for 2D TOF reconstruction. A TOF-FORE (Fourier re-binning of TOF data) algorithm is provided as an approximate re-binning algorithm obtained by extending the Fourier re-binning method for non-TOF data. In addition, two partial differential equations are identified that must be satisfied by consistent 3D TOF data, and are used to derive exact re-binning algorithms and to characterize the degree of the approximation in TOF-FORE. Numerical simulations demonstrate that TOF-FORE is more accurate than two different TOF extensions of the single-slice re-binning method, and suggest that TOF-FORE will be a valuable tool for practical TOF PET in the range of axial apertures and time resolutions typical of current scanners.

8 Claims, 6 Drawing Sheets

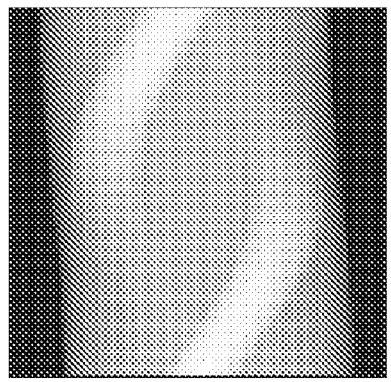
FIG. 8a
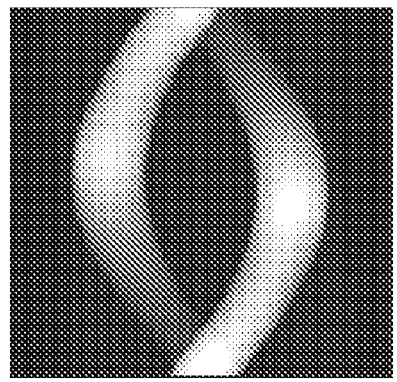
FIG. 8b
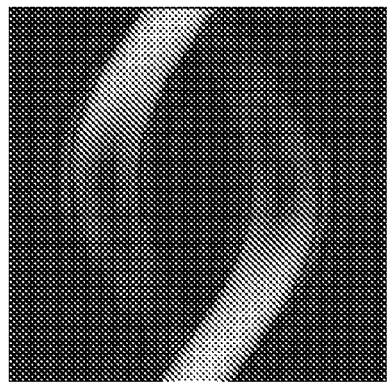
FIG. 8c
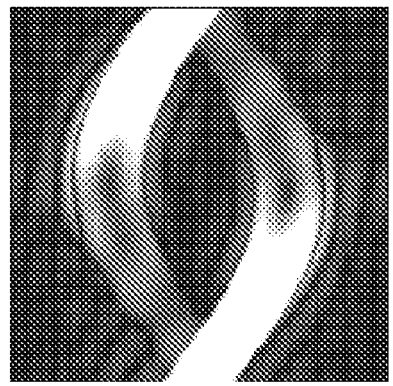
FIG. 8d
FIG. 9a "exact"
FIG. 9b TOF-FORE
FIG. 9c TOF-SSRB
FIG. 9d SSRB

FOURIER RE-BINNING OF TIME-OF-FLIGHT POSITRON EMISSION TOMOGRAPHY DATA

CLAIM OF PRIORITY FROM RELATED APPLICATION

This application claims priority under 35 U.S.C. § 119(e) from copending Provisional Application Ser. No. 60/638,532, filed Dec. 22, 2004.

FIELD OF THE INVENTION

The present invention generally relates to nuclear medicine, and systems for obtaining nuclear medicine images. In particular, the present invention relates to systems and methods for reconstructing nuclear medicine images from time-of-flight (TOF) positron emission tomography (PET) data.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred. An example of a PET method and apparatus is described in U.S. Pat. No. 6,858,847, which patent is incorporated herein by reference in its entirety.

After being sorted into parallel projections, the LORs defined by the coincidence events are used to reconstruct a three-dimensional distribution of the positron-emitting radionuclide within the patient. In two-dimensional PET, each 2D transverse section or "slice" of the radionuclide distribution is reconstructed independently of adjacent sections. In fully three-dimensional PET, the data are sorted into sets of LORs, where each set is parallel to a particular detector angle, and therefore represents a two dimensional parallel projection p(s, $\phi$) of the three dimensional radionuclide distribution within the patient, where s corresponds to the distance of the imaging plane perpendicular to the scanner axis and $\phi$ corresponds to the angle of the detector plane with respect to the x axis in (x, y) coordinate space (in other words, $\phi$ corresponds to a particular LOR direction). Coincidence events are integrated or collected for each LOR and stored as a sinogram. In this format, a single fixed point in f (x,y) traces a sinusoid in the sinogram. In each sinogram, there is one row containing the LORs for a particular azimuthal angle $\phi$; each such row corresponds to a one-dimensional parallel projection of the tracer distribution at a different coordinate along the scanner axis. This is shown conceptually in FIG. 1.

An event is registered if both crystals detect an annihilation photon within a coincidence time window $\tau$ (e.g., on the order of 4-5 ns), depending on the timing properties of the scintillator and the field of view. A pair of detectors is sensitive only to coincidence events occurring in the volume between the two detectors, thereby eliminating the need for physical collimation, and thus significantly increasing sensitivity. Accurate corrections can be made for the self-absorption of photons within the patient (i.e., attenuation correction) so that accurate measurements of tracer concentration can be made.

The number of time coincidences detected per second within a field of view (FOV) of a detector is the count rate of the detector. The count rate at each of two oppositely disposed detectors, A and B, can be referred to as singles counts, or singles, $S_A$ and $S_B$. The time required for a gamma photon to travel from its point of origin to a point of detection is referred to as the time of flight, or TOF, of the gamma photon. TOF is dependent upon the speed of light c and the distance traveled. A time coincidence, or coincidence event, is identified if the time difference between the arrival of signals in a pair of oppositely disposed detectors is less than a coincidence time window $\tau$.

As illustrated in FIG. 1, if an annihilation event occurs at the midpoint of a LOR, the TOF of the gamma photon detected in detector A ($T_A$) is equal to the TOF of the gamma photon detected in detector B ($T_B$). If an annihilation event occurs at a distance $\Delta x$ from the midpoint of the LOR, the difference between $T_A$ and $T_B$ is $\Delta t = 2\Delta x/c$, where c is the speed of light. If d is the distance between the detectors, the TOF difference $\Delta t$ could take any value from $-d/c$ to $+d/c$, depending on the location of the annihilation event.

Time-of-flight (TOF) positron emission tomography (PET) ("TOF-PET") is based on the measurement of the difference $\Delta t$ between the detection times of the two gamma photons arising from the positron annihilation event. This measurement allows the annihilation event to be localized along the LOR with a resolution of about 75-120 mm FWHM, assuming a time resolution of 500-800 ps (picoseconds). Though less accurate than the spatial resolution of the scanner, this approximate localization is effective in reducing the random coincidence rate and in improving both the stability of the reconstruction and the signal-to-noise ratio (SNR), especially when imaging large objects.

TOF scanners developed in the early 1980s were used for research and clinical applications, but the SNR gain provided by the TOF measurements of about 500 ps resolution was offset by the low stopping power of the $BaF_2$ and CsF scintillation crystals used in such scanners. Image reconstruction for complete 2D TOF-PET data has been disclosed in the prior art. Early TOF scanners used a back project-then-filter (BPF) algorithm. The maximum-likelihood estimation algorithm (MLEM) also was adapted for list-mode TOF data, and shown to provide improved image quality compared to BPF.

The increased computation required to process the TOF data also led to the proposal of a faster iterative algorithm that was directly applied to the back-projected TOF data.

In contrast with 2D TOF reconstruction, few studies have been devoted to the 3D case, probably because the rise of 3D PET in the late 1980s overshadowed the interest for TOF. The Colsher filter and the 3D re-projection algorithm for axially truncated data generalized the 3D back projection filtered methods to TOF data.

However, the spatial resolution and sensitivity offered by those TOF systems could not compete with the values achieved with BGO scanners. As a result, TOF-PET almost completely disappeared from the scene in the 1990s. Today, faster electronics and crystals such as LSO and LaBr$_3$ reopen the prospect of exploiting the TOF information without compromising other parameters such as the count rate, the sensitivity, and the energy and spatial resolutions. This prospect motivates the present invention of fast reconstruction strategies for 3D TOF-PET.

However, while extending MLEM or MAP (Maximum A posteriori Probabilitry) algorithms to 3D TOF-PET is conceptually straightforward, the computational load is an issue, because the number of data bins is now equal to the number of LORs (which exceeds $10^8$ in 3D PET even after axial undersampling using the 'span' concept) multiplied by the number of sampled TOF bins. What is needed is a feasible approach for reconstruction of 3D TOF-PET data.

SUMMARY OF THE INVENTION

The present invention solves the existing need in the art by providing a hybrid reconstruction method that re-bins the data onto a lower dimensional space and then applies a conventional 2D reconstruction. This approach requires access to either pre-corrected data or correction factors (e.g., sensitivity, random coincidences, attenuation and scatter). The hybrid method offers a good compromise between image quality and computational efficiency. The invention further makes the hypothesis that hybrid methods will also be effective for whole-body clinical TOF-PET imaging.

The first component of the hybrid approach according to the invention is the re-binning algorithm. Starting from pre-corrected TOF projection data acquired by a volume (i.e., 3D) PET scanner, a re-binning algorithm estimates for each transaxial slice the ordinary 2D data set. The re-binning algorithms according to the invention apply this procedure separately for each TOF bin, and generate for each transaxial slice a TOF data set, which can be reconstructed using any analytic or iterative algorithm for 2D TOF data.

BRIEF DESCRIPTION OF THE DRAWINGS

The invention will now be more fully described by way of example with reference to the accompanying drawings in which:

FIGS. 8(*a*)-8(*d*) show reconstructed re-binned sinograms of a cylindrical phantom, according to various re-binning algorithms; and FIGS. 9(*a*)-9(*d*) show axial sections of a stack of re-binned sinograms of a cylindrical phantom, according to various re-binning algorithms.

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

Figure 1:
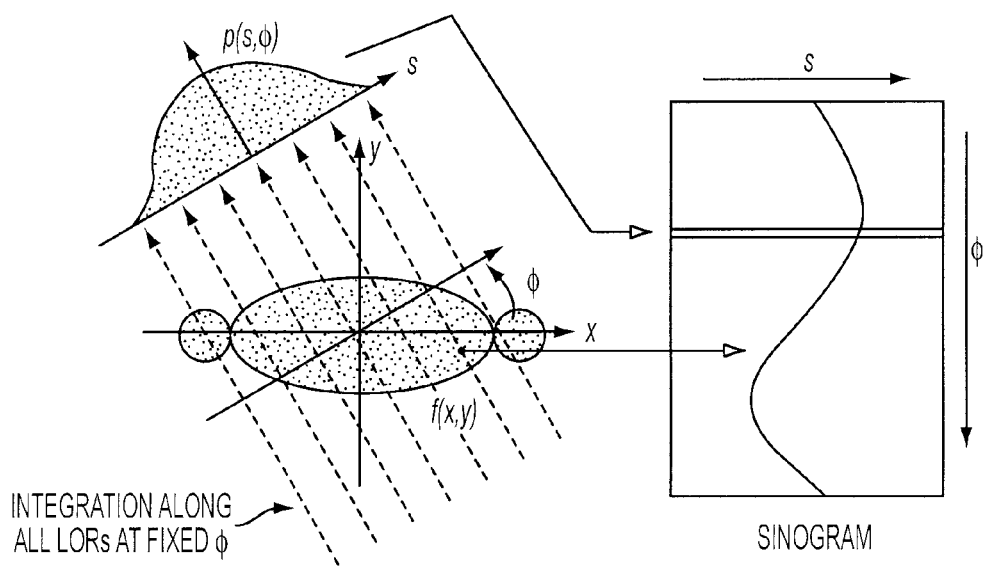
FIG. 1 is a diagram illustrating the relationship between PET projection data and a sinogram.
Figure 2:
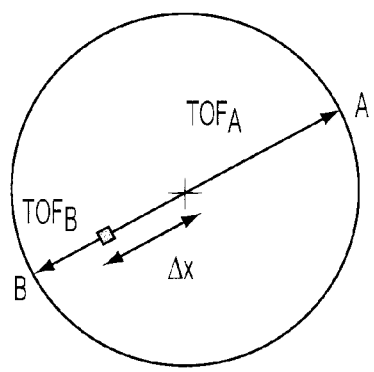
FIG. 2 is a diagram illustrating the concept of time of flight in PET imaging.
Figure 3:
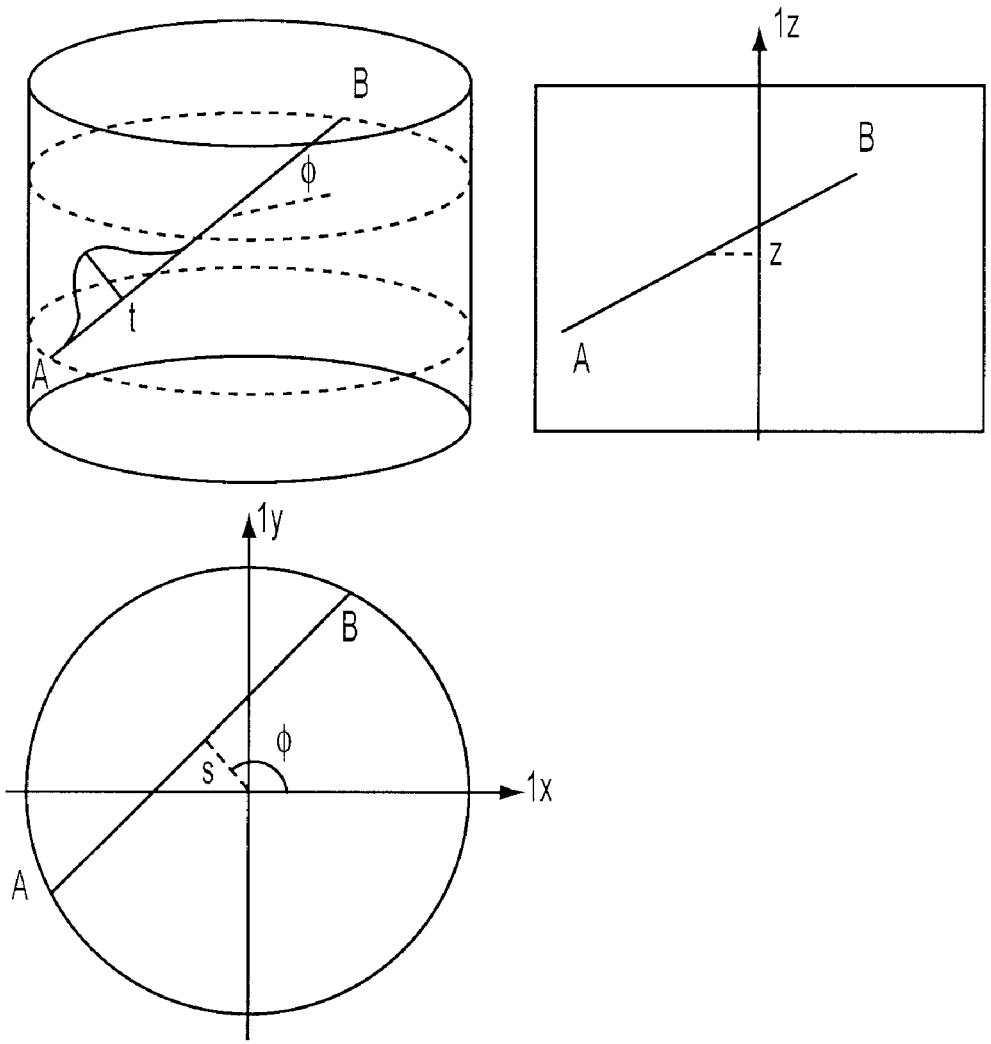
FIG. 3 is a composite diagram illustrating the parameterization of TOF-PET data in accordance with the invention.

Initially, the measured TOF data is parameterized as $$p_t^m(s, \phi, z, \delta) = \sqrt{1+\delta^2} \int_{-\infty}^{\infty} dl f(s\cos\phi - l\sin\phi, s\sin\phi + l\cos\phi, z + l\delta) h(t, l\sqrt{1+\delta^2}) \quad (1)$$

where s and $\phi$ are the usual transaxial sinogram coordinates, z is the axial coordinate of the mid-point of the LOR and $\delta = \tan\theta$ is the tangent of the angle $\theta$ between the LOR and a transaxial plane. These parameters are illustrated in FIG. 3. The range of these variables is the same as for a non-TOF scanner.

For instance, for a cylindrical scanner with radius $R_d$ and axial field of view $z \in [0,L]$, the range is $|s| \leq R_{FOV}$, $\phi \in [0, \pi)$, and $$|\delta|\sqrt{R_d^2 - s^2} \leq z \leq L - |\delta|\sqrt{R_d^2 - s^2} - \frac{L}{2\sqrt{R_d^2 - s^2}} \leq \delta \leq \frac{L}{2\sqrt{R_d^2 - s^2}} \quad (2)$$

where $R_{FOV}$ denotes the radius of the cylindrical support of f. Note that the integration variable l in equation (1) is the path length projected onto the transaxial plane, and is related to the path length r along the oblique LOR by $r = l\sqrt{1+\delta^2} = l/\cos\theta$. For a fixed pair (z, $\delta$), the function $p_t^m(s, \phi, z, \delta)$, seen as a function of s and $\phi$, is referred to as an oblique sinogram.

In equation (1) the subscript t denotes the TOF bin, corresponding to a sensitivity profile h(t, r) centered at position r=t along the LOR. The TOF parameter is related to the difference $\Delta\tau$ between the arrival times of the two photons by $t = c\Delta\tau/2$, where c is the speed of light. The re-binning algorithms according to the invention are derived for modified data defined by $$p_t(s, \phi, z, \delta) = \int_{-\infty}^{\infty} dl f(s\cos\phi - l\sin\phi, s\sin\phi + l\cos\phi, z + l\delta) h(t, l). \quad (3)$$

This parameterization is such that oblique sinograms with the same t value have the same TOF profile projected onto the transaxial plane, a property which facilitates re-binning. The simplest way to obtain the modified data is to make the approximation $$h(t,l) \cong \sqrt{1+\delta^2} h(t, l\sqrt{1+\delta^2}),$$

leading to $$p_t(s,\phi,z,\delta) \cong p_t^m(s,\phi,z,\delta) \quad (4)$$

or, alternatively, the better approximation $$h(t,l) \cong \sqrt{1+\delta^2} h(t\sqrt{1+\delta^2}, l\sqrt{1+\delta^2}),$$

leading to $$p_t(s,\phi,z,\delta) \cong p_t^m \sqrt{1+\delta 2}(s, \phi, z, \delta) \quad (5)$$

As will be seen from the numerical results presented below, these approximations are accurate when the axial aperture $\delta$ is small (e.g., smaller than 15°) and the TOF profile is sufficiently wide (e.g., a FWHM larger than 500 ps), as for typical applications with current scanners. When the TOF profile is too narrow, or the axial aperture is too large, an exact expression can be used to calculate the modified data.

The SSRB (Single Slice Re-Binning) and TOF-SSRB equations below handle each TOF bin separately and can be applied with an arbitrary TOF profile $h(t, l)$. The Fourier re-binning algorithm presented below requires merging two opposite TOF bins t and −t. This leads to a symmetry requirement $h(t, l) = h(-t, -l)$, which is normally satisfied in practice. Finally, the exact re-binning equations disclosed below are valid only for a shift invariant Gaussian profile.

The aim of a re-binning algorithm is to estimate, for each time bin t, the 2D TOF sinogram of each transaxial slice z within the axial field-of-view of the scanner. This 2D TOF sinogram is defined by $$p_{reb,t}(s,\phi,z) = p_t(s,\phi,z, 0). \quad (6)$$

The re-binned sinograms therefore can be obtained directly from equation (6), by extracting the subset of the 3D data that corresponds to $\delta=0$ (or, in practice, to $|\delta|$ smaller than some threshold). A useful re-binning algorithm, however, must incorporate the oblique sinograms for all available values of $\delta$ so as to optimize the SNR. The simplest re-binning algorithm is the straightforward extension of the single-slice re-binning (SSRB) algorithm for non-TOF data, and is based on the approximation $$p_{reb,t}(s,\phi,z) \cong p_t(s,\phi,z,\delta). \quad (7)$$

This relation is derived by neglecting the term proportional to $\delta$ in the third argument of f in equation (3). An alternative is to take advantage of the approximate TOF localization, which allows a more accurate assignment of the LOR to a specific transaxial slice. Thus, using the fact that the TOF profile is maximum at $l=t$, the variable l in the third argument of f in equation (3) can to a first approximation be replaced by t, yielding the TOF-SSRB equation, $$p_{reb,t}(s,\phi,z+t\delta) = p_t(s,\phi,z,\delta). \quad (8)$$

Contrary to equation (7), the TOF-SSRB equation (8) becomes exact when the width of the TOF profile tends to zero (in which case, however, re-binning and reconstruction are no longer needed). Once a re-binning equation has been selected, a re-binned sinogram is obtained by averaging the independent estimates provided by the redundant 3D data. For instance, if we use equation (7), $$p_{reb,t}(s, \phi, z) \simeq \frac{1}{2\delta_{\max}(z)} \int_{-\delta_{\max}(z)}^{\delta_{\max}(z)} d\delta p_t(s, \phi, z, \delta) \quad (9)$$

where $\delta_{max}(z)$ determines the range of available oblique sinograms for slice z (see equation (2)). The expression is similar for the TOF-SSRB algorithm.

The Fourier re-binning algorithm for non-TOF data was originally derived by applying the stationary phase approximation to the 2D Fourier transform of the oblique sinograms. See Defrise, Michel, A Factorization Method for the 3D x-ray Transform, *Inverse Problems*, Vol. 11, pp. 983-94 (1995). The present invention extends the derivation of the Fourier re-binning algorithm to TOF data. We assume that each sinogram characterized by z, $\delta$ and t is measured over the complete range $s\in[-R_{FOV}, R_{FOV}]$ and $\phi\in[0, 2\pi)$. Scanners usually assemble the data into sinograms with an angular range $\phi\in[0, \pi)$. Therefore, a 360° sinogram can be built by assembling two 180° sinograms, using the symmetry $$p_t(s,\phi+\pi,z,\delta) = p_{-t}(-s,\phi,z,-\delta). \quad (10)$$

This relation holds when the TOF profile is even, $h(t, l) = h(-t, -l)$, as will be assumed hereinafter. It will be noted that in contrast with the non-TOF case, two assembled 360° sinograms of opposite $\delta$ are not equivalent, and therefore $p_t(s, \phi, z, \delta)$ and $p_t(s, \phi, z, -\delta)$ yield two independent contributions to the re-binned data. To derive the Fourier re-binning approximation, we consider the 2D Fourier transform of one TOF sinogram, $$P_t(\omega, k, z, \delta) = \int_{-R_{FOV}}^{R_{FOV}} ds \int_0^{2\pi} d\phi \exp(-i\omega s - ik\phi) p_t(s, \phi, z, \delta) \quad (11)$$

where $\omega \in \Re$ is the radial frequency conjugate to s, and $k\in Z$ is the integer azimuthal frequency conjugate to $\phi$. Replacing $p_t$ by its definition (3) and transforming integration variables (s, l)→(x, y), we get $$P_t(\omega, k, z, \delta) = \int_{R^2} dxdy \int_0^{2\pi} d\phi \exp(-i\Phi(x, y, \omega, k, \phi)) \times \quad (12)$$
$$f(x, y, z + \delta(-x\sin\phi + y\cos\phi)) h(t, -x\sin\phi + y\cos\phi)$$

where the phase of the complex exponential is $$\Phi(x,y,\omega,k,\phi) = \omega(x\cos\phi + y\sin\phi) + k\phi \quad (13)$$

The stationary phase approximation is based on the observation that the phase $\phi$ varies rapidly as a function of the integration variable $\phi$ when the frequencies $\omega$ and k are large. The complex exponential $\exp(-i\phi)$ in (12) is then a rapidly oscillating sinusoid-like function. If f and h are sufficiently smooth functions of $\phi$, this behavior results in a cancellation of the $\phi$ integral over each period of the oscillation. The major contribution to the φ integral then comes from the values of φ where the phase is extremum (stationary), because the oscillations are minimized in the vicinity of these extrema. The extrema of the phase are the solutions of $$\frac{\partial \Phi(x, y, \omega, k, \phi)}{\partial \phi} = \omega(-x\sin\phi + y\cos\phi) + k = 0 \quad (14)$$

or $$-x \sin \phi + y \cos \phi = -k/\omega. \quad (15)$$

Thus, even though the values of φ for which the phase Φ is extremum do depend on x and y, they always correspond to the same position l along the LORs. To a first approximation, we can therefore replace $l = -x \sin \phi + y \cos \phi$ by $-k/\omega$ in the third argument off in equation (12):

$$P_t(\omega, k, z, \delta) \simeq \quad (16)$$

$$\int_{\mathbb{R}^2} dx\,dy \int_0^{2\pi} d\phi \exp(-i\Phi(x, y, \omega, k, \phi)) \times f\left(x, y, z - \frac{k\delta}{\omega}\right)$$

$$h(t, -x\sin\phi + y\cos\phi).$$

Noting that the TOF profile is independent of z and δ, and comparing with equation (12) at δ=0, we obtain the Fourier re-binning equation for TOF PET data, $$P_t(\omega, k, z, \delta) \simeq P_t\left(\omega, k, z - \frac{k\delta}{\omega}, 0\right). \quad (17)$$

This approximate relation is identical to the standard Fourier re-binning for non-TOF data, applied separately to each time bin t (after merging with the opposite bin $-t$ as discussed above). Re-binning is then achieved by averaging for each slice $z_0$ the estimates of $P_{reb,t}(\omega, k, z_0) = P_t(\omega, k, z_0, 0)$ provided by equation (17) for all available values of δ.

The stationary phase approximation holds asymptotically for $|\omega| \to \infty$ and $|k| \to \infty$. At low frequencies, the accuracy of equation (17) breaks down. Therefore, as in the standard Fourier re-binning algorithm, the low frequencies are re-binned using SSRB, $$P_t(\omega,k,z,\delta) \approx P_t(\omega,k,z,0) \quad (18)$$

incorporating only the smallest values of δ, for which this approximation is accurate. The efficiency of TOF-FORE stems from the empirical observation that the relation defined by equation (17) is accurate even for low frequencies, so that equation (18) needs only be used for a few frequency samples around the DC term ω=k=0.

Next, consistency conditions are derived for 3D TOF data with a Gaussian model of the TOF profile, $$h(t,l) = \exp(-(t-l)^2/2\sigma^2) \quad (19)$$

where σ, the standard deviation of the TOF profile, is related to the full-width at half-maximum $T_{FWHM}$ of the time difference measurement by $$\sigma = \frac{cT_{FWHM}}{4\sqrt{2\log 2}} \quad (20)$$

Inserting the Gaussian model (19) into equation (3), it can be shown that any function $p_t(s, \phi, z, \delta)$ that can be represented by equation (3) for some twice continuously differentiable function $f(x, y, z)$, must be a solution of the two partial differential equations, $$\frac{\partial^2 p_t}{\partial z \partial \phi} + \frac{\partial^2 p_t}{\partial s \partial \delta} = -s\delta \frac{\partial^2 p_t}{\partial z^2} - \frac{st}{\sigma^2} \frac{\partial p_t}{\partial z} + \frac{s}{\sigma^2} \frac{\partial p_t}{\partial \delta} \quad (21)$$

and $$-t\frac{\partial p_t}{\partial z} + \frac{\partial p_t}{\partial \delta} = \sigma^2 \frac{\partial^2 p_t}{\partial z \partial t}. \quad (22)$$

When $\sigma \to \infty$, the two last terms on the RHS of equation (21) vanish, and that equation reduces to John's Equation for non-TOF data (John, F., The Ultrahyperbolic Equation With Four Independent Variables, *Duke Math. J.* Vol. 4, pp. 300-22 (1938)). For simplicity we will also refer to equation (21) as "John's Equation." In the opposite limit where $\sigma \to 0$, both equation (21) (if $s \neq 0$) and equation (22) reduce to $$-t\frac{\partial p_t}{\partial z} + \frac{\partial p_t}{\partial \delta} = 0 \quad (23)$$

which is equivalent to the TOF-SSRB relation in equation (8).

The existence of two independent consistency conditions (21) and (22), instead of only one for non-TOF 3D data, can be understood by noting that four parameters are required to parameterize non-TOF data, whereas the TOF data depend on five parameters (t, s, φ, z, δ), and f(x, y, z) in both cases only depends on three parameters. Two approaches to exact re-binning will now be derived from the two consistency conditions.

We first focus on John's Equation (21), which can be applied separately to each time bin t. Taking the 2D Fourier transform of equation (21) with respect to s and φ, and using the equivalence between the derivative of a function with respect to s (or φ) and the multiplication of its Fourier transform by iω (or ik), leads to the following equation for the function Pt(ω, k, z, δ) defined in (11):

$$k\frac{\partial P_t}{\partial z} + \omega\frac{\partial P_t}{\partial \delta} = -\delta \frac{\partial^3 P_t}{\partial \omega \partial z^2} - \frac{t}{\sigma^2} \frac{\partial^2 P_t}{\partial \omega \partial z} + \frac{1}{\sigma^2} \frac{\partial^2 P_t}{\partial \omega \partial \delta}. \quad (24)$$

An exact re-binning algorithm similar to the FOREJ algorithm described in "Fast Rebinning Algorithm for 3D PET Using John's Equation," Defrise, M. and Liu, X., *Inverse Problems*, Vol. 15, pp. 1047-65 (1999), is obtained by considering a fixed (ω≠0, k), and by noting that the LHS of equation (24) is the directional derivative of $P_t$ along the vector (k, ω) in the plane (z, δ). In this plane a line segment $z = z_0 + k\delta/\omega$, $0 \leq \delta \leq \delta_1$, is defined, which links a point $(z_1 = z_0 + (k/\omega)\delta_1, \delta_1 \neq 0)$, corresponding to some measured oblique sinogram, to a point $(z_0, 0)$ corresponding to the 2D sinogram of slice $z_0$. Along this line segment, equation (24) is written as $$\frac{dP_t(\omega, k, z_0 + k\delta/\omega, \delta)}{d\delta} = -\frac{1}{\omega} \quad (25)$$

$$\left(\delta \frac{\partial^3 P_t}{\partial \omega \partial z^2} + \frac{t}{\sigma^2} \frac{\partial^2 P_t}{\partial \omega \partial z} - \frac{1}{\sigma^2} \frac{\partial^2 P_t}{\partial \omega \partial \delta}\right)\left(\omega, k, z_0 + \frac{k\delta}{\omega}, \delta\right).$$

Integrating between $\delta=0$ and $\delta=\delta_1$ leads to the exact re-binning equation $$P_t(\omega, k, z_0, 0) = P_t(\omega, k, z_1, \delta_1) - \quad (26)$$

$$\int_0^{\delta_1} d\delta \frac{dP_t(\omega, k, z_0 + k\delta/\omega, \delta)}{d\delta}$$

$$= P_t(\omega, k, z_0 + k\delta_1/\omega, \delta_1) +$$

$$\frac{1}{\omega}\int_0^{\delta_1} d\delta \left(\delta \frac{\partial^3 P_t}{\partial \omega \partial z^2} +\right.$$

$$\left.\frac{t}{\sigma^2} \frac{\partial^2 P_t}{\partial \omega \partial z} - \frac{1}{\sigma^2} \frac{\partial^2 P_t}{\partial \omega \partial \delta}\right)$$

$$\left(\omega, k, z_0 + \frac{k\delta}{\omega}, \delta\right).$$

As in the previous section, re-binning is achieved by averaging for each slice $z_0$ the estimates of $P_{reb,t}(\omega, k, z_0) = P_t(\omega, k, z_0, 0)$ provided by (26) for all available values of $\delta_1$.

If the axial aperture $\delta$ is sufficiently small, and the standard deviation $\sigma$ of the TOF profile is sufficiently large, the RHS of equation (25) can be neglected. At this, approximation the Fourier transformed sinogram $P_t$ is constant along the line $z=z_0+k\delta/\omega$, the integral on the RHS of equation (26) disappears and equation reduces to equation (17). This alternative derivation of TOF-FORE shows that the approximation error has contributions of order $O(\delta^2/\omega)$ and of order $O(\delta/\sigma^2\omega)$.

An alternative approach to exact re-binning is based on the second consistency condition (22). Consider a fixed $(s, \phi)$ and define in the plane $(z, \delta)$ a line segment $z=z_0-t\delta$, $0 \leq \delta \leq \delta_1$, which links a point $(z_1=z_0-t\delta_1, \delta_1 \neq 0)$, corresponding to some measured oblique sinogram, to a point $(z_0, 0)$ corresponding to the 2D sinogram of slice $z_0$. The directional derivative of $p_t$ along this line is $$\frac{dp_t(s, \phi, z_0 - t\delta, \delta)}{d\delta} = \left(-t\frac{\partial p_t}{\partial z} + \frac{\partial p_t}{\partial \delta}\right)(s, \phi, z_0 - t\delta, \delta) \quad (27)$$

$$= \sigma^2 \frac{\partial^2 p_t(s, \phi, z_0 - t\delta, \delta)}{\partial z \partial t}$$

where we have used the consistency condition (22); Integrating between $\delta=0$ and $\delta_1$ leads to $$p_t(s, \phi, z_0, 0) = \quad (28)$$

$$p_t(s, \phi, z_0 - t\delta_1, \delta_1) - \sigma^2 \int_0^{\delta_1} d\delta \frac{\partial^2 p_t(s, \phi, z_0 - t\delta, \delta)}{\partial z \partial t}.$$

A few differences with the first exact re-binning, equation (26), are worth noting:

Re-binning is applied directly to the sinograms, without requiring a 2D Fourier transform.

The TOF sampling should be sufficiently fine to allow an accurate calculation of the partial derivative with respect to t.

The TOF-SSRB equation (8) is obtained by neglecting the integral on the RHS of equation (28), which is an approximation of order $O(\sigma^2\delta)$. This shows that the accuracy of TOF-FORE and of TOF-SSRB have opposite behaviors when the TOF resolution improves. For the relatively poor timing resolution achievable with current detectors, TOF-FORE appears preferable, as demonstrated by the numerical results below.

TABLE 1

| Simulation parameters. | |
| --- | --- |
| Ring radius (mm) | 278 |
| Number of rings | 32 |
| Maximum ring difference used | 29 |
| Span | 1 |
| Number of Oblique sinograms | 1018 |
| tan $\theta_{max}$ (degree) | 14 |
| Ring spacing (mm) | 4.8 |
| Radial sampling (mm) | 1.2 |
| Number of radial s samples | 256 |
| Number of angular $\phi$ samples | 256 |
| Digitized phantom | 256 × 256 × 63 |
| voxel size (mm) | 1.2 × 1.2 × 2.4 |

The TOF-FORE algorithm has been evaluated using simulated data for a multi-ring scanner described by the parameters in table 1. Experimentally, TOF data (with a time resolution of around 1.2 ns) are sorted in multiple time bins (e.g. 9 bins of 500 ps) to cover the whole FOV (4.5 ns=675 mm). In this simulation, we examine TOF data with a Gaussian profile of FWHM 75 mm or 120 mm, centered at t=50 mm. This corresponds to a time resolution of 500 ps or 800 ps at $\Delta\tau$=300 ps. Noise free 3D TOF sinograms were simulated according to equation (1), by forward projecting the digitized image of two phantoms (without attenuation or scatter). The modified 3D TOF data (3) were then obtained using the approximation (4).

The oblique sinograms were re-binned with SSRB, TOF-SSRB and TOF-FORE. For TOF-FORE the low-frequency samples $(i_\omega, k)$ satisfying $|i_\omega| \leq i_{max}=6$ and $|k| \leq k_{max}=6$ were re-binned using SSRB with a maximum ring difference $rd_{max}=4$. The re-binned 2D sinograms were compared to the 'exact' 2D sinograms $p_{exact,t}(s, \phi, z)$ obtained by forward projecting the digitized phantom with the same TOF profile. For each slice, a normalized root-mean-square (RMSE) difference between the re-binned sinogram and the 'exact' sinogram was calculated as $$RMSE[z] = \left(\frac{\int ds \int d\phi (p_{reb,t}(s, \phi, z) - p_{exact,t}(s, \phi, z))^2}{\max_z \int ds \int d\phi p_{exact,t}(s, \phi, z)^2}\right)^{1/2}. \quad (29)$$

For comparison, non-TOF data of the two phantoms were also simulated and re-binned with the standard FORE algorithm, using the same parameters $i_{max}$, $k_{max}$ and $rd_{max}$ for the low frequency region. The RMSE was then calculated according to (29) (normalization is important because the sinogram values are smaller for the TOF data, due to multiplication by the TOF profile (19)).

Figure 4:
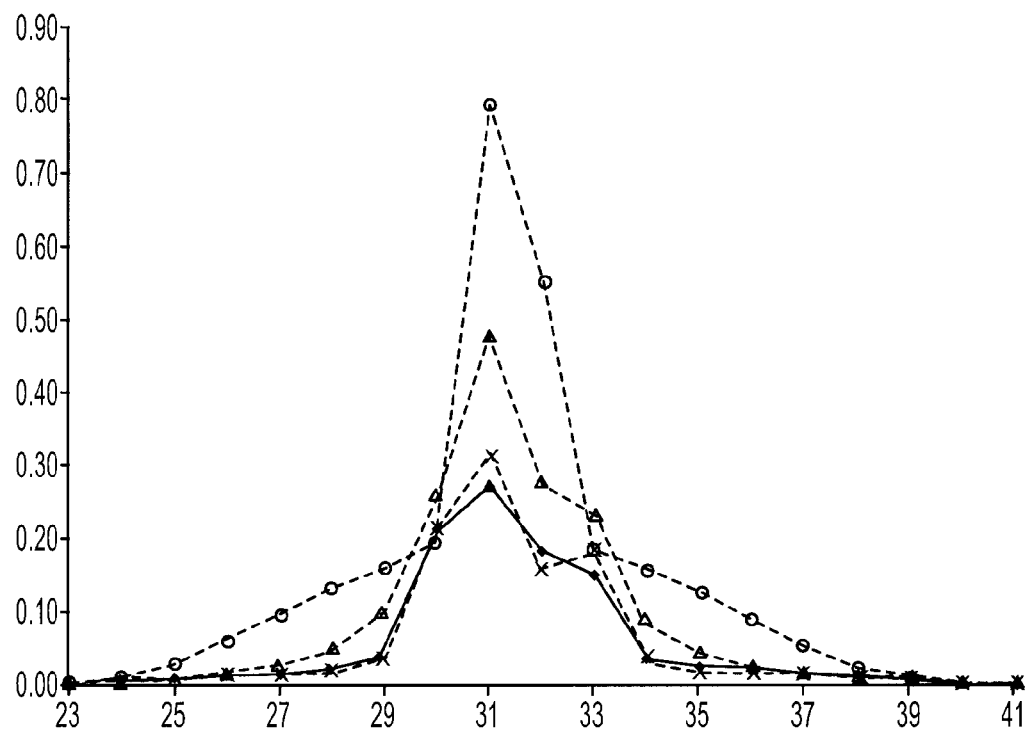
FIG. 4 is a graph illustrating normalized RMS error for re-binned sinograms of an ellipsoid phantom as a function of slice index, for a number of re-binning algorithms.
Figure 5:
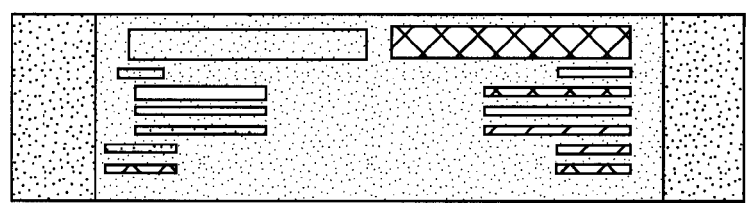
FIG. 5 is a diagram illustrating a cross-section of a cylindrical phantom as used in simulations in accordance with the invention.
Figure 6:
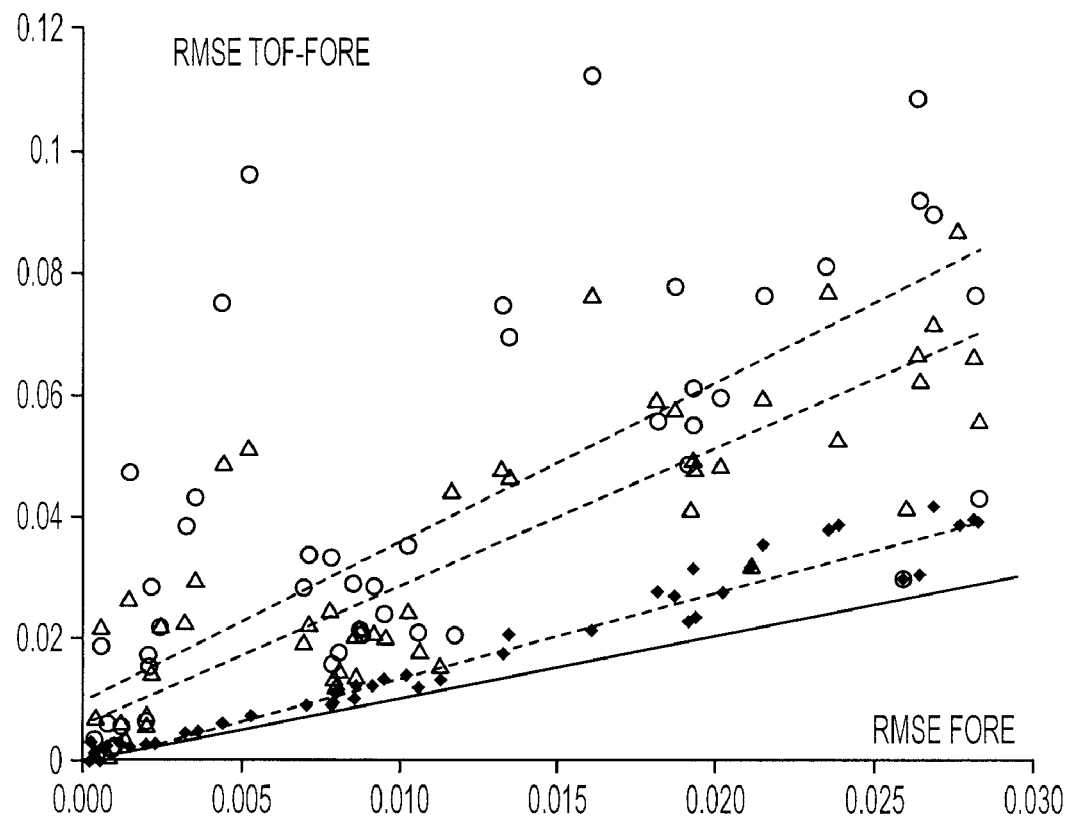
FIG. 6 is a graph illustrating normalized RMS error for re-binned sinograms of the cylindrical phantom at a FWHM of 120 mm.

The first phantom is an ellipsoid with uniformly distributed activity, centered at (x, y, z)=(56,−76, 75) mm with semi-axis (20, 30, 3) mm. The center of this object is not aligned axially with the center of a reconstructed slice. FIG. 4 shows the RMSE difference between the re-binned and the exact sinograms, as a function of the axial slice. The second phantom is a combination of 20 cylinders of various sizes and intensities, inside a larger cylinder of radius 120 mm (see FIG. 5). For this phantom, the RMSE was normalized with the root-mean-square of each slice (i.e. using equation (29) without the $max_z$). FIG. 6 shows the RMSE for the various algorithms with FWHM=120 mm, plotted versus the normalized RMSE for the non-TOF data re-binned with FORE. On the average, the error with TOF-FORE is a factor 1.38 larger (slope of the regression line) than the non-TOF reference (solid line in FIG. 6). The error does not exceed 5% and is significantly smaller than with the two SSRB algorithms. As with the ellipsoid phantom, using the TOF information in SSRB significantly improves the accuracy, as shown in Table 2 below.

TABLE 2

Figure 7:
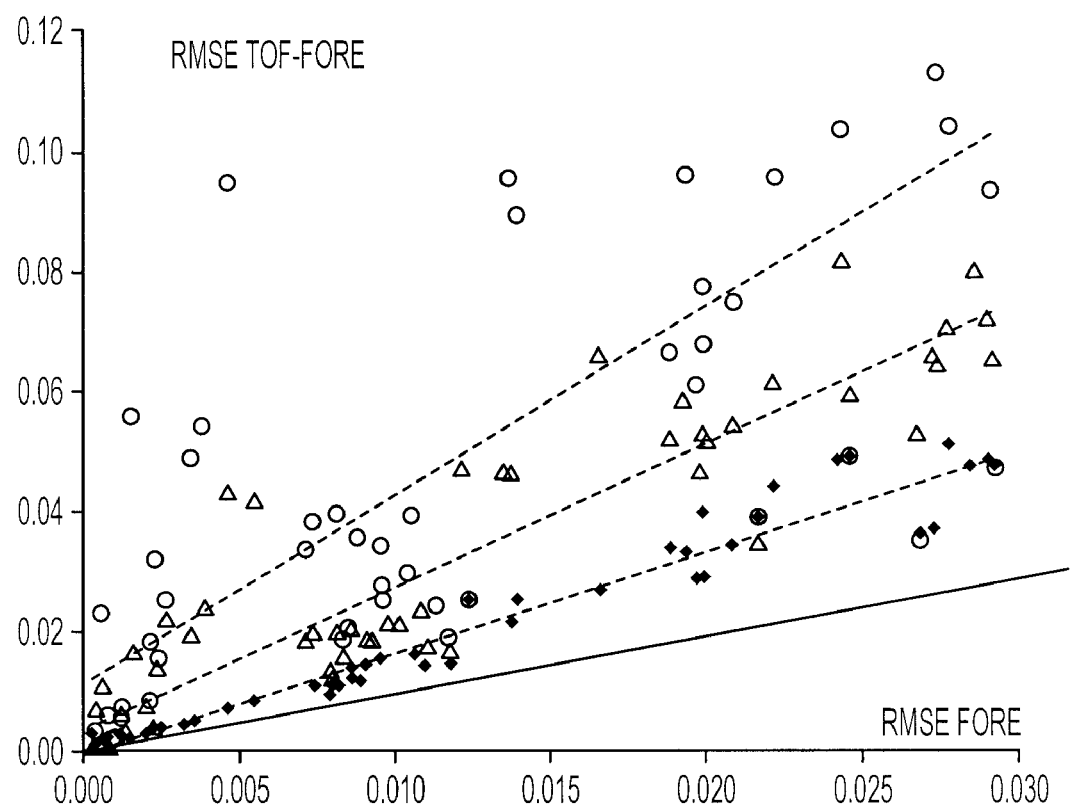
FIG. 7 is a graph illustrating normalized RMS error for re-binned sinograms of the cylindrical phantom at a FWHM of 75 mm.

Equations of the regression lines in FIGS. 6 and 7

|  | FWHM = 75 mm | FWHM = 120 mm |
|---|---|---|
| SSRB | y = 3.23x + 0.012 | y = 2.62x + 0.009 |
| TOF-SSRB | y = 2.46x + 0.002 | y = 2.26x + 0.006 |
| TOF-FORE | y = 1.71x + 0.000 | y = 1.38x + 0.000 |

As expected from the analysis of John's equation above, the accuracy of TOF-FORE decreases when the TOF resolution improves. For instance, for a FWHM of 75 mm (FIG. 7), the error with TOF-FORE is a factor 1.71 larger than the non-TOF reference, instead of 1.38 with a FWHM of 120 mm. FIGS. 8(a)-(d) and 9(a)-(d) illustrate the structure of the re-binning error for this phantom.

In FIGS. 8(a)-(d), the re-binned sinogram $i_z$=32 of the cylindrical phantom is obtained from TOF data with FWHM=120 mm. FIG. 8(a) shows the "exact" sinogram. The absolute error for the TOF-SSRB re-binning, scaled to 10% of the maximum of the "exact" sinogram, is shown in FIG. 8(b). The absolute error for TOF-FORE, scaled to 10%, is shown in FIG. 8(c). The same absolute error for TOF-FORE, scaled to 2% to elicit low-level artifacts, is shown in FIG. 8(d).

FIGS. 9(a)-(d) illustrate an axial section of the stack of re-binned sinograms for the cylindrical phantom with TOF data (FWHM=120 mm), respectively for the "exact" sinogram, the TOF-FORE re-binding, TOF-SSRB re-binning, and SSRB re-binning. The section shown corresponds to s=−84 mm. The vertical axis is the axial slice coordinate z and the horizontal axis is the angle φ. Grey scale range [0.40M, M], where M is the maximum value in the 'exact' axial section.

In summation, measuring and exploiting time-of-flight information in 3D PET has considerable potential, especially for whole-body imaging of large patients, an application where improvement would have an important clinical impact. The present invention provides a way to accelerate the reconstruction of 3D TOF data through Fourier re-binning. The TOF-FORE algorithm is provided to generate a good approximation of "exact" 2D TOF sinograms and shown to be superior to TOF-SSRB when the timing resolution is larger than 500 ps and the axial aperture does not exceed 15°.

Simulation results demonstrate that TOF-FORE can be a valuable method for PET scanners with TOF capability: the timing resolution achievable with current detector technology is larger than 1 ns, and in this case the accuracy of TOF-FORE is comparable to the accuracy of the FORE algorithm.

The present invention further provides two partial differential equations that must be satisfied by consistent TOF-PET data. These two equations lead to two different exact re-binning algorithms, which provide insight into the accuracy of the TOF-FORE and TOF-SSRB algorithms, both of which were shown to be first-order approximations to the exact re-binning.

The five dimensional data space in 3D TOF-PET results in a very rich structure which was only partially elicited and exploited here by the derivation of the two consistency conditions. It will be apparent to those skilled in the art from the present disclosure that more efficient re-binning algorithms, which would better combine the measured TOF information with the 'virtual' TOF information provided by the stationary phase approximation, may be achieved by further analysis of the 3D TOF-PET data structure.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A method for reconstructing a nuclear medical image from TOF-PET imaging data, comprising the steps of:

obtaining three dimensional TOF-PET data from a PET scanner;

storing said TOF-PET data in a plurality of TOF time bins, each bin corresponding to a time difference value of photons arriving at opposite detectors of said PET scanner;

estimating, for each time bin, a two dimensional TOF sinogram of each transaxial slice z within an axial field of view of said scanner, by averaging independent estimates of redundant three dimensional TOF-PET data; and reconstructing an image from said estimated two dimensional TOF sinograms using a two dimensional TOF reconstruction algorithm.

2. The method of claim 1, wherein said three dimensional TOF-PET data is represented by the following equation:

$$p_t^m(s, \phi, z, \delta) = \sqrt{1+\delta^2} \int_{-\infty}^{\infty} dl f(s\cos\phi - l\sin\phi, s\sin\phi + l\cos\phi, z + l\delta) h(t, l\sqrt{1+\delta^2}).$$

3. The method of claim 2, wherein the step of estimating comprises the step of modifying said three dimensional TOF-PET data to $$p_t(s, \phi, z, \delta) = \int_{-\infty}^{\infty} dl f(s\cos\phi - l\sin\phi, s\sin\phi + l\cos\phi, z + l\delta) h(t, l).$$

4. The method of claim 3, wherein said modified data is estimated as $$p_{reb,t}(s,\phi,z+t\delta)=p_t(s,\phi,z,\delta).$$

5. The method of claim 4, wherein said two dimensional TOF sinogram is obtained by solving for the equation $$p_{reb,t}(s, \phi, z) \simeq \frac{1}{2\delta_{\max}(z)}\int_{-\delta_{\max}(z)}^{\delta_{\max}(z)}d\delta p_t(s, \phi, z, \delta).$$

6. The method of claim 5, wherein said two dimensional TOF sinogram is obtained by solving for the equation $$P_t(\omega, k, z, \delta) \simeq P_t\left(\omega, k, z - \frac{k\delta}{\omega}, 0\right).$$

7. The method of claim 5, wherein said two dimensional TOF sinogram is obtained by solving for the equation $$P_t(\omega, k, z_0, 0) = P_t(\omega, k, z_1, \delta_1) - \int_0^{\delta_1} d\delta \frac{dP_t(\omega, k, z_0 + k\delta/\omega, \delta)}{d\delta}$$

$$= P_t(\omega, k, z_0 + k\delta_1/\omega, \delta_1) +$$

$$\frac{1}{\omega}\int_0^{\delta_1} d\delta\left(\delta\frac{\partial^3 P_t}{\partial\omega\partial z^2} + \frac{t}{\sigma^2}\frac{\partial^2 P_t}{\partial\omega\partial z} - \frac{1}{\sigma^2}\frac{\partial^2 P_t}{\partial\omega\partial\delta}\right)$$

$$\left(\omega, k, z_0 + \frac{k\delta}{\omega}, \delta\right).$$

8. The method of claim 5, wherein said two dimensional TOF sinogram is obtained by solving for the equation $$p_t(s, \phi, z_0, 0) = p_t(s, \phi, z_0 - t\delta_1, \delta_1) - \sigma^2\int_0^{\delta_1} d\delta\frac{\partial^2 p_t(s, \phi, z_0 - t\delta, \delta)}{\partial z\partial t}.$$

* * * * *